United States Patent
Haagensen et al.

(10) Patent No.: US 6,751,364 B2
(45) Date of Patent: Jun. 15, 2004

(54) IMAGE ANALYSIS SYSTEMS FOR GRADING OF MEAT, PREDICTING QUALITY OF MEAT AND/OR PREDICTING MEAT YIELD OF AN ANIMAL CARCASS

(75) Inventors: Peter Haagensen, deceased, late of McCook Lake, SD (US), by Annett Haagensen, legal representative; Horst Eger, Ahrensfelde (DE); Mohammed Koohmaraie, Clay Center, NE (US); Steven D. Shackelford, Clay Center, NE (US); Tommy L. Wheeler, Harvard, NE (US)

(73) Assignee: Tyson Fresh Meats, Inc., Dakota Dunes, SD (US)

( * ) Notice: Subject to any disclaimer, the term of this patent is extended or adjusted under 35 U.S.C. 154(b) by 240 days.

(21) Appl. No.: 09/977,641

(22) Filed: Oct. 15, 2001

(65) Prior Publication Data

US 2003/0072472 A1 Apr. 17, 2003

(51) Int. Cl.$^7$ .................................................. G06K 9/22
(52) U.S. Cl. ....................................... 382/313; 382/110
(58) Field of Search ................................. 382/312, 313, 382/321, 324, 100, 110, 128; D16/200, 208, 209; 348/89; 452/158; 426/231

(56) References Cited

U.S. PATENT DOCUMENTS

| | | | |
|---|---|---|---|
| 3,154,625 A | 10/1964 | Kail .............................. 88/14 |
| 4,413,279 A | 11/1983 | Gorl ............................ 358/107 |
| 4,414,546 A | * 11/1983 | Taylor et al. ............. 340/825.3 |
| 4,939,574 A | 7/1990 | Petersen et al. ............... 358/93 |
| 5,079,951 A | 1/1992 | Raymond et al. ............. 73/602 |
| 5,194,036 A | 3/1993 | Chevalier et al. ........... 452/198 |
| 5,339,815 A | 8/1994 | Liu et al. ............... 128/660.01 |
| 5,470,274 A | 11/1995 | Kadi et al. .................. 452/184 |
| 5,668,634 A | 9/1997 | Newman ..................... 356/445 |
| 5,793,879 A | 8/1998 | Benn et al. .................. 382/110 |
| 5,872,314 A | 2/1999 | Clinton ........................ 73/602 |
| 5,944,598 A | 8/1999 | Tong et al. .................. 452/158 |
| 6,198,834 B1 | 3/2001 | Belk et al. ................... 382/110 |

OTHER PUBLICATIONS

Shackelford, S.D., Coupling of Image Analysis and tenderness Classification to Simultaneously Evaluate Carcass Cutability, Longissimus Area, Subprimal Cut Weights, and Tenderness of Beef; *Journal of Animal Science*, 1998, 2631–2640; vol. 76; U.S. Department of Agriculture, Clay Center, NE, USA.

(List continued on next page.)

*Primary Examiner*—Andrew W. Johns
(74) *Attorney, Agent, or Firm*—Mark E. Stallion; Blackwell Sanders Peper Martin, LLP

(57) ABSTRACT

The invention is an image analysis system and method for grading of meat, predicting quality of meat and/or predicting meat yield of an animal. One embodiment of the invention is particularly designed to capture an image of the $12^{th}$ rib cross section of the ribeye and perform an image analysis of the ribeye for grading purposes. The image capturing camera portion of the system has a wedged shaped camera housing for ease of insertion into the ribbed incision. The image capturing portion of the system further comprises a camera with a flash for consistent lighting. The camera is positioned such that it views the ribeye cross section at an angle to accommodate the wedge shape of the camera housing for ease of insertion in the incision. The camera housing also has various alignment means to facilitate the user's ability to capture images in a consistent manner. Once the image is captured either digitally or captured and converted to a digital image, an image analysis is performed on the digital image to determine parameters such as the percentage lean, total area of the ribeye, total fat area, total lean area, percent marbling, and thickness of fat adjacent to the ribeye, and other parameters. These parameters are used to predict value determining traits of the carcass.

13 Claims, 6 Drawing Sheets

OTHER PUBLICATIONS

Shackelford, Steven, D., Wheeler, Tommy, L., Koohmaraie, Mohammad, Marc Tenderness Classification System; *Proceedings of the 1997 Meat Industry Research Conference*, 19–25; U.S. Department of Agriculture, Clay Center, NE, USA.

Cross, H.R., Gilliland, D.A., Durland P.R., Seideman, S. Beef Carcass Evaluation By Use of Video Image Analysis System, *Journal of Animal Science*, 1983; 908–917, vol. 57, No. 4; U.S. Department of Agriculture, Clay Center, NE, USA.

Wassenberg, Reneel., Allen D.M., Kemp, K.E. Video Image Analysis Prediction of Total Kilograms and Percent Primal Lean and Fat Yeild of Beef Carcasses; *Journal of Animal Science*, 1986; 1609–1616, vol. 62; U.S. Department of Agriculture, Clay Center, NE, USA.

\* cited by examiner

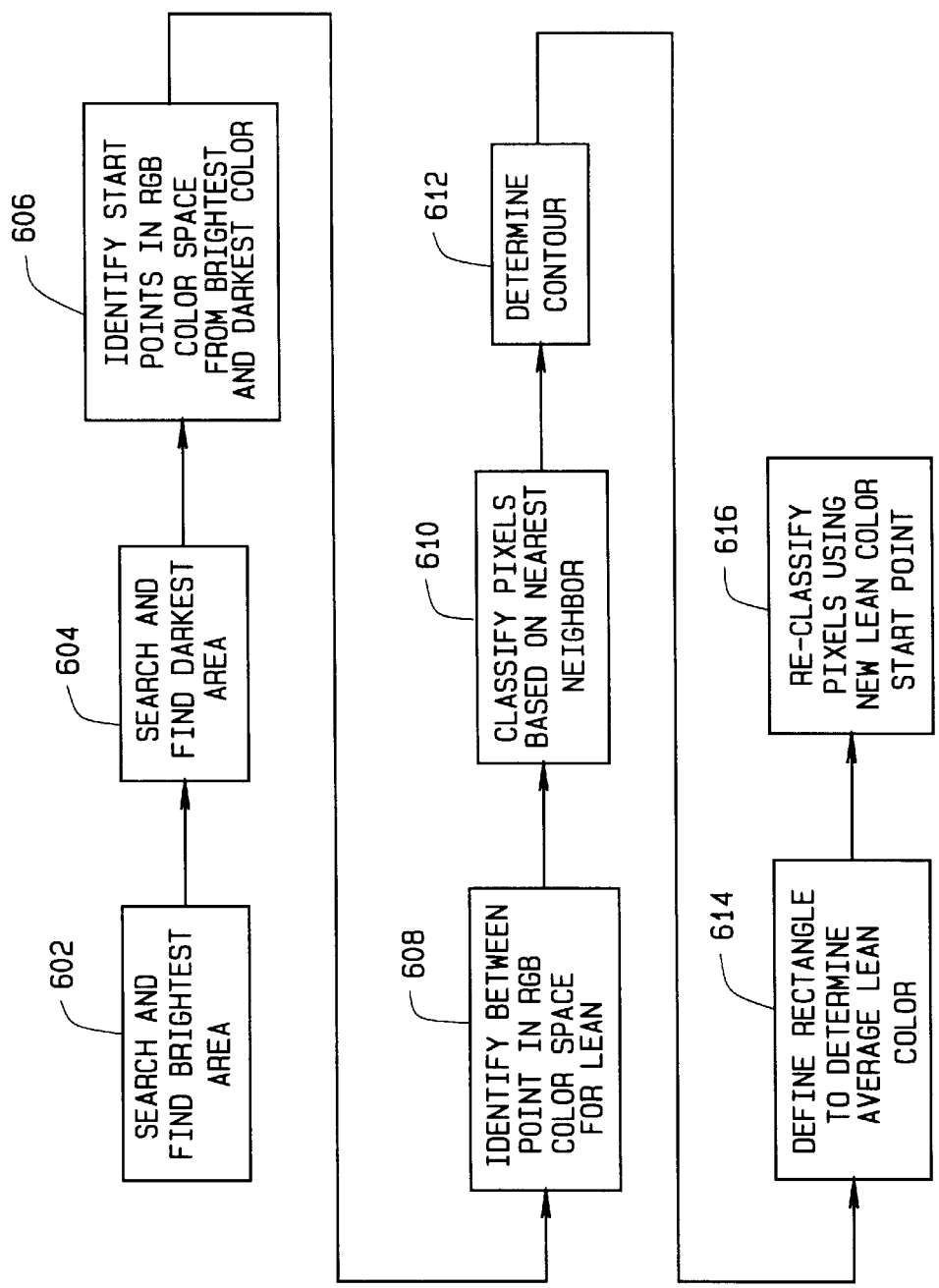

ns. The ri ection of ribbed sec and 13th ribs thereby exposing for examination and grading a cross section of meat or a cutting surface of meat, which specifically includes the ribeye and associated subcutaneous fat. For quality grade, the human grader will typically examine the 'marbling' (intramuscular fat). For yield grade, the human grader will typically examine the area of the ribeye cross section and the thickness of subcutaneous fat adjacent to the ribeye at various points around its area and adjust the fat thickness based on fatness of the entire carcass. For yield grade, the human grader also utilizes parameters such as hot carcass weight and percentage kidney, pelvic and heart fat for determining yield grade.

IMAGE ANALYSIS SYSTEMS FOR GRADING OF MEAT, PREDICTING QUALITY OF MEAT AND/OR PREDICTING MEAT YIELD OF AN ANIMAL CARCASS

BACKGROUND OF INVENTION (1) Field of Invention

The invention relates to automated grading of meat and predicting meat yield and quality of meat from an animal carcass and, more particularly, to capturing images of meat portions of an animal carcass and processing information in the image for grading of meat and predicting meat yield.

(2) Background Art

Grading of animal carcasses for the purpose of predicting meat yield and quality is an important aspect of the meat processing industry. Meat grading has historically been performed by a human grader. To perform the meat grading process the human grader will typically examine key physical aspects of the carcass. The type of grading being performed determines what physical aspects of the carcass need to be examined by the grader. The two main types of meat grading for a carcass are quality grade and yield grade. The quality grade describes the meat's palatability or tenderness. Whereas, yield grade describes the proportion of lean boneless meat that a given carcass will yield.

In the meat industry, it is common for the human grader to examine various physical aspects of a cross section of the Longissimus dorsi (commonly referred to in beef as the 'ribeye' and in pork as the 'loin eye') for both yield grading and quality grading. In a typical beef processing facility after the animal has been slaughtered, head removed and skinned, the carcass is further disassembled by splitting the carcass in half along the midline. The carcass is then 'ribbed' or severed between the twelfth $12^{th}$ and $13^{th}$ ribs thereby exposing for examination and grading a cross section of meat or a cutting surface of meat, which specifically includes the ribeye and associated subcutaneous fat. For quality grade, the human grader will typically examine the 'marbling' (intramuscular fat). For yield grade, the human grader will typically examine the area of the ribeye cross section and the thickness of subcutaneous fat adjacent to the ribeye at various points around its area and adjust the fat thickness based on fatness of the entire carcass. For yield grade, the human grader also utilizes parameters such as hot carcass weight and percentage kidney, pelvic and heart fat for determining yield grade.

Grading by a human grader is typically based upon the human grader's perception of the appearance of the ribeye. Photographs can be utilized as standards for determining grade. Photographs are used for training for quality grade, but are not typically used for grading. This process clearly introduces a substantial amount of subjectivity into the meat processing industry. The Human Grader's subjectivity is problematic because this grading determines the valuation of animal carcasses and therefore clearly effects the financial bottom line.

Yield grade is typically denoted by a numerical value from 1 to 5 based upon the yield from the carcass of boneless, closely trimmed (approximately 0.25 in.), retail cuts from the round, loin, rib and chuck. An accurate yield grade for these four wholesale cuts of meat is extremely important to an accurate valuation of the carcass, thus reducing the amount of subjectivity is desirable. These four wholesale cuts make up approximately 75% of the weight, and about 90% of the carcass value. Regression equations for carcass grading have been developed from actual carcass data using factors such as fat thickness at the twelfth ribeye cross section, ribeye area and carcass weight. However, the regression equations are not practical for a human grader to utilize during actual everyday grading of a carcass in a production facility. Therefore, working formulas have been developed which make certain adjustments to the yield grade based on the same type of factors utilized by the regression equations. However, this process still results in a substantial amount of subjectivity.

In order to reduce operator subjectivity, automated instrumental grading systems have been developed. For example, various type of image analysis grading systems have been developed, which capture and analyze digital images of portions of a carcass. The image analysis systems typically examine parameters similar to or identical to the type of parameters examined by a human grader. Typically the image analysis systems try to determine and distinguish portions that are lean and portions that are fat and their respective areas. To distinguish meat portions (i.e. lean or fat; ribeye muscle or non-ribeye muscle surrounding ribeye) the image analysis system will typically utilize parameters such as color and contrast.

It is typical for the image analysis to be performed on the $12^{th}$ ribeye cross section. However, regardless of the section of meat that is being analyzed, there are various problems in utilizing image analysis to characterize the features of the meat. For example, the muscle or the lean area of interest can be surrounded by other lean areas with minimal fat separation, which is typically true of a ribeye cross section. Therefore, it is often difficult for the image analysis system to distinguish between the muscle of interest and the adjacent muscle because the dimensions and shape of a given muscle type may vary considerably from carcass to carcass. Another example is that a muscle of a given carcass may have large areas of intramuscular fat, whereas that same muscle type for another carcass may not have the large area of intramuscular fat. This is problematic because it is difficult due to the intramuscular fat to determine where the desired muscle ends and the adjacent muscle begins. Dense marbling can also make it difficult to determine the border or the cross section area of the muscle of interest. Yet another example is distinguishing color transitions from fat to lean. Color distinction is critical particularly with dense marbling and large areas of intramuscular fat because digital analysis algorithms often look for continuous adjacent pixels of the same color to determine if a red or lean region of the image is within the area of the desired muscle. Due to the above problems many image analysis systems have difficulty identifying the correct area of the desired muscle and then appropriately analyzing the image.

Image analysis of the ribeye poses unique problems particularly in a production meat processing environment where the ribbed carcass halves are graded for quality and yield. In a typical production meat processing facility, particularly beef processing, the halved and ribbed beef carcass travels through the grading area suspended from a conveyor hook by the achilles tendon. The ribbed section of the carcass partially exposes the $12^{th}$ rib cross section. The cross section is not fully exposed for ease of viewing because the ribbing incision is minimized such that the carcass stays intact. If the ribbing incision is too deep the head portion of the carcass will separate from the hind portion due to weight and gravity. Therefore, due to the minimized incision, it is sometimes difficult even for the human grader to get a clear view of the cross section for grading purposes without physically manipulating the carcass to obtain a better view. It is even more difficult to insert a camera in the incision to capture a good image consistently that has adequate lighting, minimal shading, and with minimal angular distortions of the image. Obtaining a good and consistent image must be achieved prior to even addressing the problems of image analysis identified above. However, obtaining a high quality image is difficult and most systems are inadequate, particularly with the inconsistent and non-uniform lighting found in most facilities.

BRIEF SUMMARY OF INVENTION

The invention is an image analysis system and method for grading of meat, predicting quality of meat and/or predicting meat yield of an animal carcass. One embodiment of the invention is particularly designed to capture an image of the $12^{th}$ rib cross section of the carcass side and perform image analysis of the ribeye for grading purposes. The image capturing camera portion of the system has a substantially wedged shaped camera housing for ease of insertion into the ribbed incision. The image capturing portion of the system further comprises a camera with a flash for consistent lighting. The camera is positioned such that it views the ribeye cross section at an angle to accommodate the wedge shape of the camera housing for ease of insertion in the incision. The camera housing also has various alignment means to facilitate the user's ability to capture images in a consistent manner. Once the image is captured either digitally or captured and converted to a digital image, an image analysis is performed on the digital image to determine parameters such as the total area of the ribeye, total fat area, total lean area, percent marbling, and thickness of subcutaneous fat adjacent to the ribeye. The image analysis algorithm performs multiple steps to obtain the desired parameters. The steps include, geometrical correction for angular distortions particularly due to the wedge shaped camera housing, shading correction, image flip when processing the compliment (right) side of carcass, first adaptive color segmentation for fat and lean color distinction, erosion and dilation, second adaptive color segmentation and contour determination. The adaptive color segmentation is one novel aspect of the invention that provides for distinct color separation for lean and fat thereby facilitating defining the total ribeye area, total fat area, total lean area and percent marbling.

BRIEF DESCRIPTION OF DRAWINGS

For a better understanding of the present invention, reference may be made to the accompanying drawings.

FIG. 6 is a detailed flow diagram of the color segmentation portion of the algorithm.

DETAILED DESCRIPTION OF INVENTION

Figure 1:
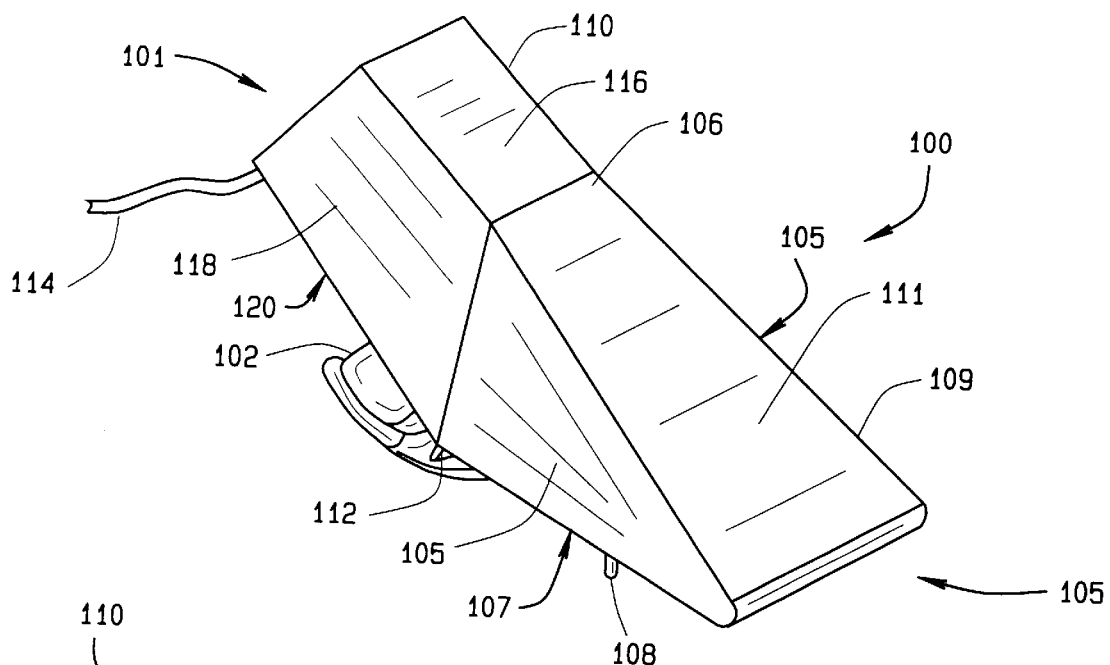
FIG. 1 is a perspective view of the image capturing camera assembly.

According to the embodiment(s) of the present invention, various views are illustrated in FIGS. 1–7 and like reference numerals are being used consistently to refer to like and corresponding parts of the invention for all of the various Figs. of the drawing. The first digit(s) of the reference number for a given item or part should correspond to the Fig. Number in which the item or part is first identified.

The present invention is an image analysis system and method for grading of meat, predicting quality of meat and/or predicting meat yield of an animal carcass. This system and method is designed to be utilized in a meat processing facility, specifically those related to beef processing. The system and method is designed to capture an image of an exposed ribeye cross section of a halved ribbed beef carcass. The system is specifically designed to enable the user to consistently capture a quality image of the ribeye cross section by inserting a wedged-shape camera into the incision of the ribbed carcass. Once the image is captured, the present invention performs an image analysis of the digitized image for grading of the beef carcass. The following description and drawing should clarify the detailed operation of at least one embodiment of the invention.

Referring to FIG. 1, a perspective view of the image capturing camera assembly is shown. The image capturing camera assembly 100 is designed with a substantially wedge-shaped form factor to facilitate insertion into the ribbed incision. The image capturing camera comprises an ergonomically designed handle 102 which further comprises a trigger or switch communicably linked to the camera and flash, not seen in this view, refer to FIG. 2, item 212, for triggering the shutter of the camera for capture of the image with the camera and also triggering or flashing the camera flash.

Figure 2:
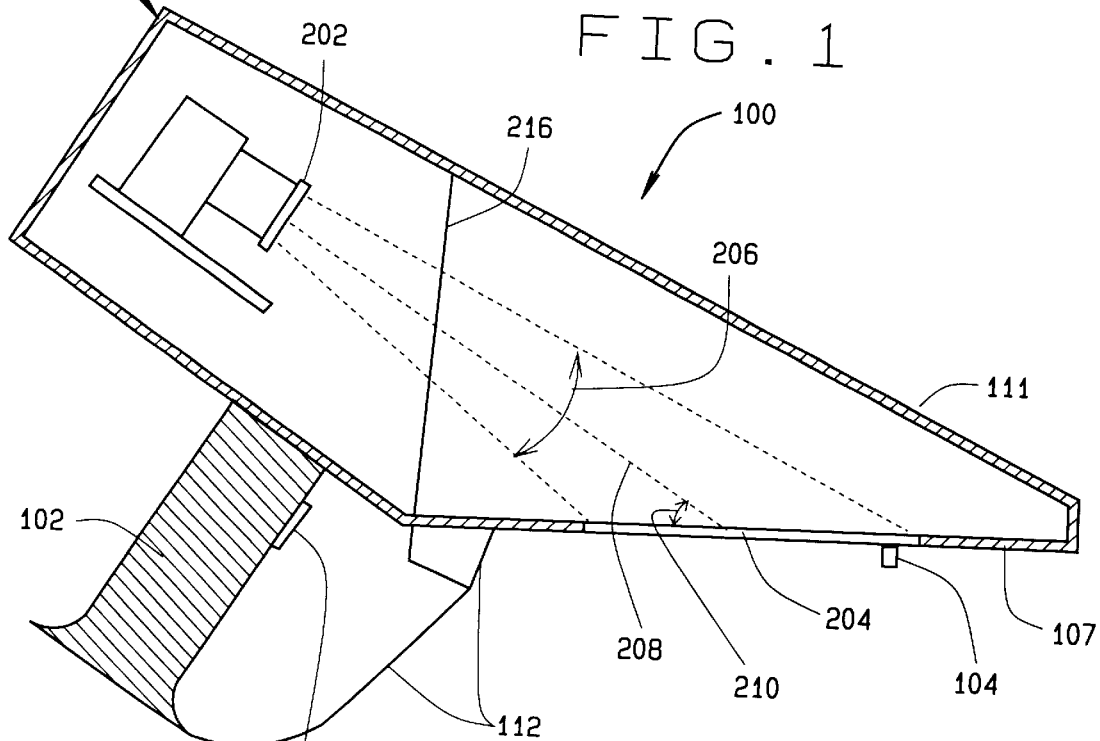
FIG. 2 is a side cross sectional view of the image capturing camera.
Figure 3:
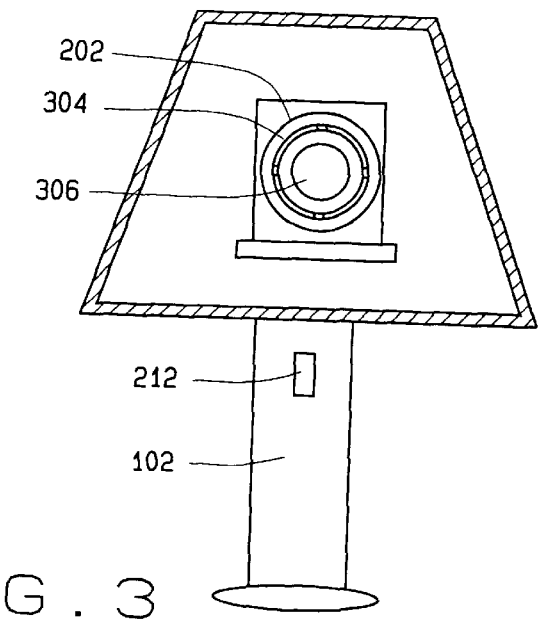
FIG. 3 is a front cross sectional view of the image capturing camera.

The image capturing camera assembly 100 has a substantially wedge-shaped housing 106 having a height that tapers from a taller back end 101 to a shorter front end 103. The taper is formed by a tapered or sloped top, and the bottom is substantially flat. The bottom has an opening or viewing window designed for positioning over a ribeye cross section or other meat part for viewing and capturing an image. One embodiment shown in FIGS. 1–3 is a two-piece housing design comprising a front nose portion 109 and a rear portion 110. The rear portion 110 of the housing is where the camera is housed and mounted and the front nose portion 109 is for insertion into the incision of the ribbed carcass. For the embodiment shown in FIGS. 1–3, the nose portion is generally a polyhedron having a substantially wedge-shaped form factor. The top 111 and bottom 107 of the nose portion of the housing intersect forming a blunt edge such that there is an oblique dihedral angle between the top and bottom giving the nose portion a substantially wedge shape. The nose portion further comprises an opening or viewing window on the bottom. The sides 105 of the nose portion are canted inwardly toward one another from bottom to top in order to facilitate the user's viewing around the camera housing. One benefit of a separate front nose portion is the ease of removing and cleaning.

The front nose portion is firmly attached to the rear portion 110 where the camera is mounted and the handle 102 is attached. The rear portion also has a generally polyhedron form factor. The rear portion is attached to the front nose portion in such a manner that the camera mounted therein is angled downward directing its field of view toward the opening or viewing window on the bottom side of the front nose portion. The top 116 of the rear portion is generally aligned with the top 111 of the front nose portion to provide a substantially consistent taper to the overall top. The sides 118 of the rear portion are canted inward toward one another from bottom to top similar to the sides 105 of the front nose portion. The bottom 120 of the rear portion forms an oblique dihedral angle with the bottom side 107 of the front nose portion to assist in achieving the appropriate angle of the camera mounted therein. The camera and its mounting can also provide a portion of or all of the desired angling. The resulting form factor of the overall two-piece housing is a substantially wedge-shaped form factor. The camera wedge-shaped housing is designed to form a hood over the camera assembly including, camera, camera flash and electronics so that the field of view includes only the object of interest and standardizes the distance between the camera lens and the object of interest. The housing 106 is designed with a large enough opening such that the camera has a full view of the ribeye cross section. The hood or housing 106 has a substantially wedge shape such that is can be easily inserted into the ribbed carcass and adequately aligned. The housing 106, in addition to having an overall wedge shape top to bottom, also has inwardly tapered sides 105, 118 in order to reduce the size of the housing while not obstructing the field of view of the camera. The tapered sides are designed to improve the user's view of the ribeye.

The camera housing design has other alignment features that facilitate the user's ability to repetitively capture high quality (high definition, clarity, sharpness) images. For example, the camera housing is flat on the side of the opening. This flat underside or bottom 107 of the camera housing allows the user to place the camera housing flush and flat against the cutting surface and particularly against the surface of the ribeye cross section so that the appropriate viewing angle of the camera is achieved when the image is captured. Another example of an alignment feature for the camera housing is the first and second stud guide extensions 108, 104 (104 not shown in this view, see FIG. 2) on either side of the opening or viewing window of the camera housing and the studs extend below the exterior surface of the bottom for side to side positioning. These stud guides facilitate a consistent alignment of the camera by preventing side-to-side motion of the camera.

The camera housing also has a backstop guide extension or an alignment plate 112 which should consistently control the depth of insertion of the camera into the incision of the ribbed carcass for capturing an image of the ribeye. This guide provides for front to back alignment and as shown one embodiment of the guide extends below the bottom surface. The camera housing can be inserted into the incision until the backstop guide abuts the edge of the incision. The camera assembly 100 also has a communication line 114 capable to carry digitized images that have been captured. The camera opening or viewing window can be rectangular in shape and large enough to encompass the entire ribeye cross section. The rectangular opening or viewing window also defines a field of view obtainable by the camera. The front nose portion of the housing can be further designed to have an upper hood portion, which is removably attached to the base portion. If a transparent material is utilized for the viewing window or if there is simply an opening, the removable upper hood portion facilitates cleaning.

Referring to FIG. 2, a side cross sectional view of the image capturing camera assembly 100 is shown. The cross sectional view reveals the angular positioning of the camera 202 for optimal viewing through the opening 204 or viewing window of the housing. The positioning of the camera to view the ribeye cross section is driven by the wedge-shaped housing design and the position of the viewing window 204. The angle of the camera also minimizes back reflections into the lens of the camera. The downward canted angle of the camera is such that field of view 206 of the camera is canted downward and the viewing angle 208 creates an oblique angle of incidence 210 at the viewing window such that almost all reflections from the attached camera flash will travel away from the lens and be absorbed by the substantially non-reflective interior of the camera housing. This is particularly important if a transparent material, such as glass, covers the opening, however, the viewing window can simply be an opening. If the viewing window is simply an opening, a transparent material such as glass can be installed over the opening of the rear portion 110 vertically along seam 216. This material will isolate the camera and electronics from contaminants. Also, if a transparent material is installed along seam 216. The camera 202 can be moved closer to the transparent material to avoid reflection back into the lens. This configuration has advantages in that the transparent material does not make contact with the object for which an image in being captured. The viewing angle and field of view are angled such that the field of view of said camera at least subtends the entire view of the viewing window 204 such that an image of the cutting surface seen through the viewing window is fully captured.

The camera can be a digital camera. The digital camera utilized can be any type of color digital camera providing adequate resolution. A color analog camera can also be utilized but the analog image must be digitized by a frame grabber function which requires additional camera circuitry. Optionally, the frame grabber circuitry can be part of an image analysis computing system in lieu of being part of the camera circuitry. The camera can also be designed with a camera image output operable to output an image captured by the camera for input to an image analysis computing system.

Referring to FIG. 3, a front cross sectional view of the image capturing camera assembly is shown. One embodiment of the invention is shown with a camera 202 having a circular camera flash 304 that extends around surrounding the lens 306 of the camera. The circular flash design provides for uniform lighting when the image is being captured. To obtain uniform lighting, the camera flash need not be circular. The camera flash can optionally extend substantially around the lens of the camera. For example, the flash could have multiple flash element segments which substantially surround the lens in a substantially symmetrical pattern.

For prevention of glare due to the flash, the opening to the housing can optionally be covered with a glare resistant window made of glass or some other transparent material. The window prevents undesired material getting inside the camera housing through the opening. The window is removably mounted over the opening such that it can be removed for cleaning. Also, as discussed above, the housing is preferably a two-piece housing comprising a rear portion and a front nose portion, where both the front nose portion and rear portion can each optionally have an upper hood portion and base portion, where the upper hood portion of the housing is removably mounted to the lower base portion of the housing. The ability to remove the upper hood portion of the housing allows for the upper hood portions to be removed such that the assembly can be readily cleaned. The special housing design of the camera shelters the camera from the surrounding ambient light environment. The housing provides for a self-contained environment for capturing an image of the ribeye. This self-contained environment, along with the camera flash, provides adequate uniform lighting for the camera when capturing the image. The housing also limits the field of view of the camera.

Figure 4:
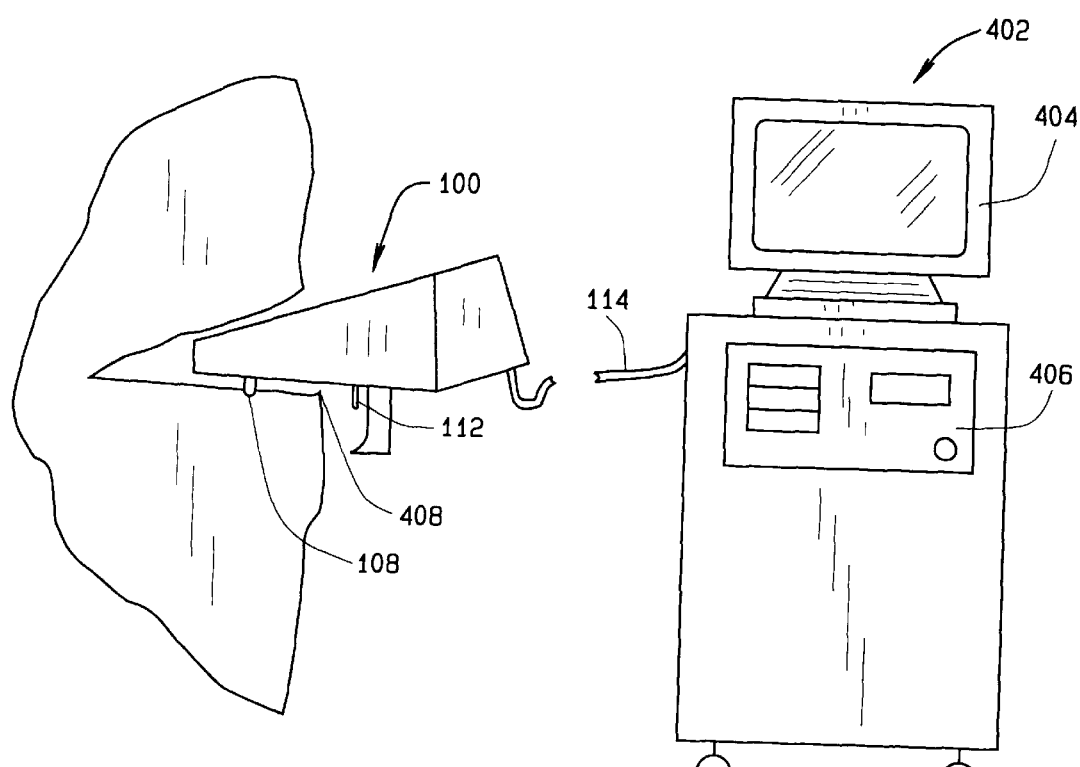
FIG. 4 is a functional diagram of the overall system.

Referring to FIG. 4, a functional diagram of the overall image analysis system is shown. The system comprises the image capturing camera assembly 100 as described in FIGS. 1–3 for capturing an image of the ribeye cross section. The camera contained therein could be an analog camera or a digital camera. However, if an analog camera is utilized, additional circuitry is required to digitize the image prior to, or subsequent to transmitting the image to the image analysis computing station 402. The image capturing camera has a camera image output integral with communication line 114 for transmitting the image out to an image analysis, computing system. The image analysis computing station performs the image analysis function by executing an image analysis algorithm. The execution of the image analysis algorithm analyzes the image and identifies various parameters that are utilized for grading the carcass. The algorithm then grades the carcass based on the parameters identified. A monitor 404 can also be communicably linked to the image analysis computing station by way of a CPU 406 for displaying the image captured. The algorithm can be further operable to display the image on a monitor in a color coded format to identify the various lean portions and fat portions of the image. The system can also present a real time image on the monitor as seen by the camera when the user is positioning the camera over the ribeye, which may facilitate positioning the camera to assure the entire ribeye is in the image. Stud guide extensions 108 and backstop guide 112 are also used for alignment. The stud guide extension can be positioned on either side of the cutting surface for side-to-side alignment. The front end nose portion of the camera housing assembly can be inserted into the incision until the backstop guide 112 abuts the edge 408 of the incision. The stud guides and backstop guide can be positioned such that when the camera assembly is inserted in the ribbed incision, the viewing window is positioned relative to the ventral side of the ribeye and the same features of the cross section are consistently captured. For example, the viewing window can be positioned in a medial lateral direction. The image and the related data can also be stored on the image analysis computing station for future reference. The image analysis computing station can be a customized computing station or any personal computer with adequate processing and memory to perform the image analysis function.

Figure 5:
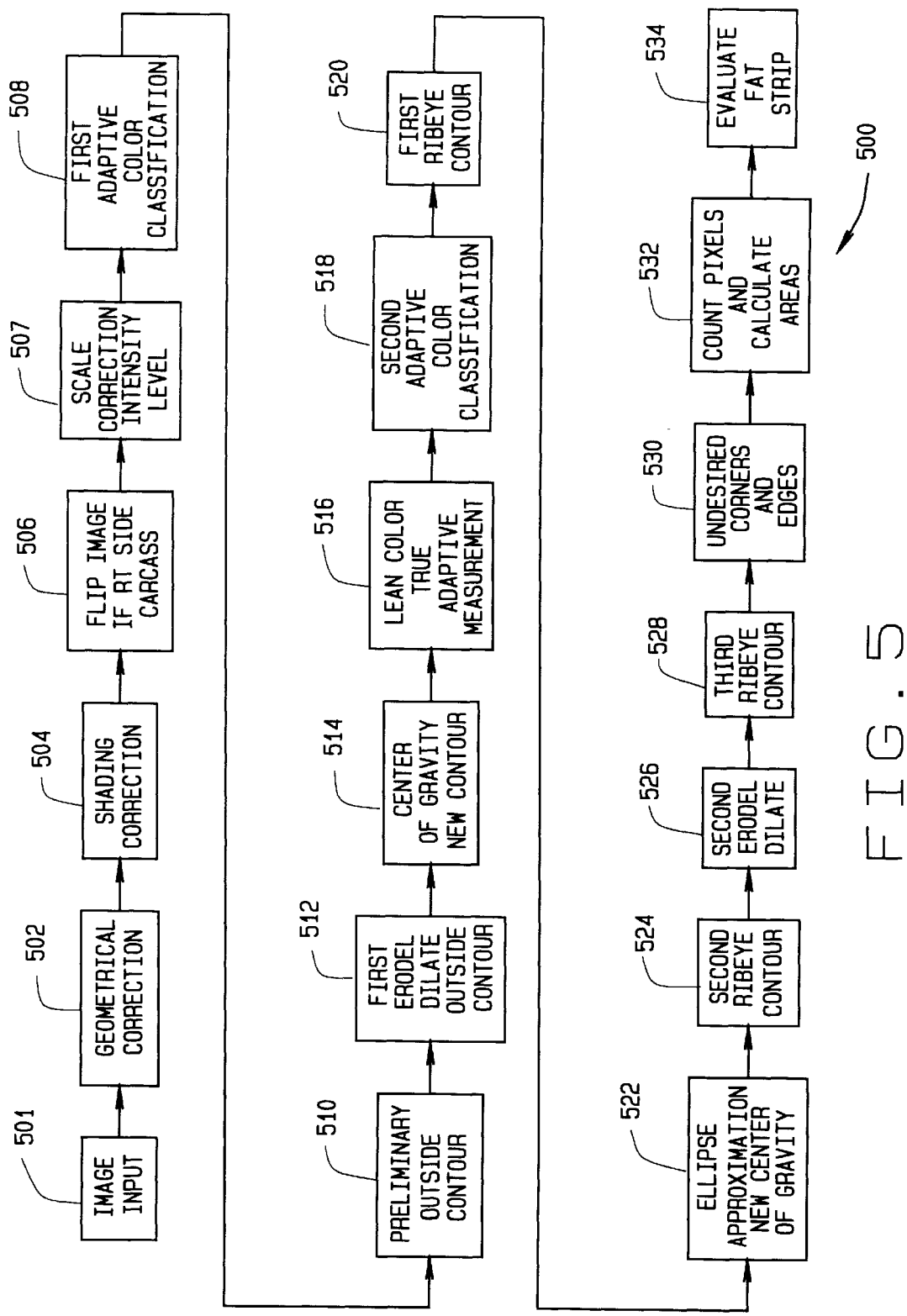
FIG. 5 is a flow diagram of the image analysis algorithm.

Referring to FIG. 5, a flow diagram 500 of the image analysis algorithm is shown. The image analysis algorithm performs a method for grading a beef carcass. The method as shown in FIG. 5 accommodates the camera design by correcting geometric distortions, shading and intensity. One embodiment of the camera design creates a geometric distortion because the image is captured at an oblique angle. Intensity and shading anomalies also result from the angle of camera and the housing design. Based on the design of the camera, the image has distortion in the x and y directions. The reason for the angle is the acute wedge shape of the housing and the position of the viewing window. Due to the housing, the camera is angled downward such that its field of view can subtend the viewing window. The substantial wedge shape of the housing is ideal because it provides a very small nozzle like end of the unit which can be inserted in the incision and placed on the ribeye even if the ribbing incision is improper. The shading anomaly occurs because a camera flash light is used to provide good contrast between the ribeye and the background image. However, due to the angle between the light and the ribeye surface light shading in the image results. The level of intensity in certain areas of the image may have anomalies for the same reasons. Therefore, both the distortion and the shading have to be corrected.

The image input functional block 501 is operable to input the image from the image capturing system or camera.

The geometrical correction functional block 502 is representative of the functional step for correcting the image due to angular distortion caused by the viewing angle of the camera. A mathematical correction of the image based on the known angle of the camera transforms the image to correct the x and y directional distortion. The parameters for this transformation can be used for every image taken by the camera. Methods for correcting x and y directional distortions are well known in the art. For example, an image can be captured of grid lines contrasted against a white background with the camera assembly. The grid lines are parallel in both the x and y directions and spaced an equal distance apart. When the image is captured, the grid lines are distorted in both the x and y directions. A mathematical algorithm can be developed to correct the grid lines in the image. This algorithm can be utilized to correct other images.

The shading correction functional block 504 is representative of the step of correction for shading anomalies. A mathematical correction of the image transforms the shading image into an approximately equally intense image over the complete image area. Methods for correcting for shading anomalies are well known in the art. For example, an image can be captured of a white uniform background with the camera assembly. When the image is captured, shading anomalies will likely result. A mathematical algorithm can be developed to correct the shading returning the image to a uniform white. This algorithm can be utilized to correct other images. The parameters are predetermined based on the angle of the camera and flash and the shape of the housing for the shading correction and these parameters can be used for every image taken by the camera.

The flip image if right carcass side (compliment side) functional block 506 is representative of the step that flips the image if a compliment side carcass is being examined. For one embodiment of the invention the algorithm can be designed to work with ribeyes of a left carcass side. If there is a right carcass side the image can be flipped and the analysis works as it would for a left carcass side. Methods are well known in the art for distinguishing an image from its compliment or in this case distinguishing an image of the left carcass side from an image of the compliment right carcass side. For example, an algorithm can be developed to distinguish between the direction of a given taper of a portion of an object and its compliment. See U.S. Pat. No. 5,944,598. issued Aug. 31, 1999 to Tong et al.

The scale correction to pre defined intensity level functional block 507 is representative of the function to correct overall intensity and contrast. The image is scaled to a pre defined intensity while maintaining or improving the relative contrast. The area is analysed for the pixels with the highest intensity. If the intensity of these pixels are lower than a predefined level where said predefined level is optimized for a given camera's flash, resolution and contrast ratio, then the whole image is transformed in a way that the highest intensity pixel has the pre defined intensity level and all other pixels with lower intensities are linearly transformed to their corrected relative intensity. This step improves images with low light by increasing the contrast and brightness.

The first adaptive colour classification functional block 508 performs the first color segmentation step for the image. The aim of the colour classification function is to separate and categorize the pixels of the image into a component of Background (almost black), Fat (almost white) or Lean (almost red) in a three dimensional colour space R,G,B (red, green, blue). To establish the three start points in the RGB color space for the respective colour classifications, the brightest and darkest areas in the image will be analyzed and the lightest area will be analyzed to establish the start point for fat and the darkest area will be analyzed to establish a start point for the Background. Analyzing the darkest and lightest areas to establish the respective start points can be as simple as determining the darkest or lightest pixel or pixels within the respective areas and using as a start point or determining the center of gravity of each of the respective areas and using as a start point. Also, please note that the lightest and/or the darkest areas can be as small as a single pixel if the algorithm is so designed. The start point for the lean will be estimated in this first adaptive colour classification step to be between the two start points of fat and Background (for example, 0.5 of the vector distance between the two points). Once the three start points are established, the nearest neighbour method is utilized to decide for each point or pixel of the image if it is a point of the class Background, Fat or Lean. If a pixel has nearly the same distance between two of the start points for instance between fat and lean then that pixel is classified as unknown. Classifying the pixels having nearly the same distance as unknown is necessary because for some meat cuts the overall color range of fat may overlap with the color range of lean, thus, the difference between the distances to the start points may be too close to classify. For example, a criterion could be if the shorter distance is not less than 80% of the longer distance, then the distances are considered nearly the same and the pixel is classified as unknown. After the first color classification step is performed all pixels are sorted (or classified) in the four classes background, lean, fat or unknown.

The preliminary outside contour functional block 510 performs the step of determining a first preliminary outside contour. The result of the first color classification step is utilized to analyze the outside contour of the cutting surface. This function is performed by examining each pixel coming inward from the image border and determining if there is a gradient between a pixel of the class Background with a neighbor pixel which is not background (lean, fat or unknown). Each gradient point establishes an outside contour point. A successful completion of this step establishes a starting point for the contour analysis. Each pixel coming inward from the image border is examined pixel by pixel for the same gradient once around the complete object such that the result gives the outside contour.

The first erode and dilate functional block 512 represents the erosion and dilation steps to further define the contour. Once the first preliminary outside contour has been established an erosion and dilatation of this preliminary outside contour is performed to eliminate little attachments on the outside contour like fat, bone or lean parts. This step is performed by iteratively eroding the contour by iteratively shrinking the outside contour a pre determined number of times to a contour inside the last contour (erode) and after that by enlarging with same number of iterations a contour outside the last contour. One method of eroding the outside contour is to iteratively erode the exterior most pixels that form the last outside contour pixel-by-pixel and layer-by-layer a predetermined number of times. The number of times is determined and optimized based on the resolution of the camera, the typical overall area of the meat cut being examined, the typical area of surrounding fat and surrounding lean, and the typical number and size and contours of lean. For example, a camera having a moderate resolution of 768×572 pixels can require 10 times erosion when analysing a typical ribeye. Dilation is then performed the same number of times by dilating pixels immediately adjacent the last contour. After the dilation step, little attached parts are excluded from the preliminary outside contour of the cut surface to establish a new outside contour. Various erosion/dilation techniques that are well known in the art can be utilized.

The centre of gravity of the new outside contour functional block 514 is representative of the step to determine the center of gravity of the new outside contour. The center is located nearly always in the ribeye.

The measurement of actual lean color functional block 516 is representative of the step to determine the true adaptive start point for lean color in the ribeye, which is the second adaptive color classification. Around the center of gravity a rectangular subarea can be measured with a predetermined size. Defining this predetermined size subarea to have a rectangular geometry can be done for simplicity, however, a subarea having any geometry can be used. The size of the rectangle (or subarea having any other geometry) is determined and optimized based on the resolution of the camera, the size of the object or meat being examined and what is reasonably large enough to obtain a good sampling for color determination yet staying within the area of the object or meat of interest. For example, for a camera having a resolution of 768×572 pixels capturing a ribeye image, a rectangle sized which will encompass 50×50 pixels can be sufficient. The adaptive start point for the color of the lean is then determined by only measuring the color of pixels in that rectangle, which have a color classification class "Lean". In other words, all pixels with the class Fat or Unknown within that rectangular are not used to calculate the average lean color. This is very important in cases where within the rectangle there is a lot of marbling or the rectangle is somewhat located in a fat area (can happen on very fat animals). With this method it doesn't matter because only lean pixels are considered.

The second adaptive color classification output functional block 518 is representative of taking the adaptive start points and calculating certain parameters because now an adaptive start point for the lean is established rather than the previous estimate in the first adaptive color classification. The first color classification only provided adaptive start points for fat and Background. The classification itself is the same method as previously performed but with full adaptive start points. This adaptive classification gives us the final segmentation of the cutting surface into background, lean, fat and unknown.

The following parameters can now be calculated by a classification area function in this step:

total area of cut surface total lean area total fat area total unknown area

The determination of a first ribeye adaptive contour functional block 520 starts from the center of gravity examining the pixels looking for a gradient between lean and fat/unknown/background using the adaptive color classification now established. The gradient searched for is between lean to something else (non-lean). Once a start point is established the method goes around the object to analyze the contour thereby defining the first ribeye contour. If the resulting contour is too small to be a ribeye we look further until we find a contour with reasonable size. The limits (min and max) are predetermined adaptively based on the size of the preliminary outside contour. Deciding whether a contour is too small can be determined by comparing the size of the preliminary outside contour to what the typical ribeye size is for a cut surface having a given preliminary outside contour. This step is needed to be assured that it is the ribeye contour and not the contour of an adjacent muscle.

Figure 5A:
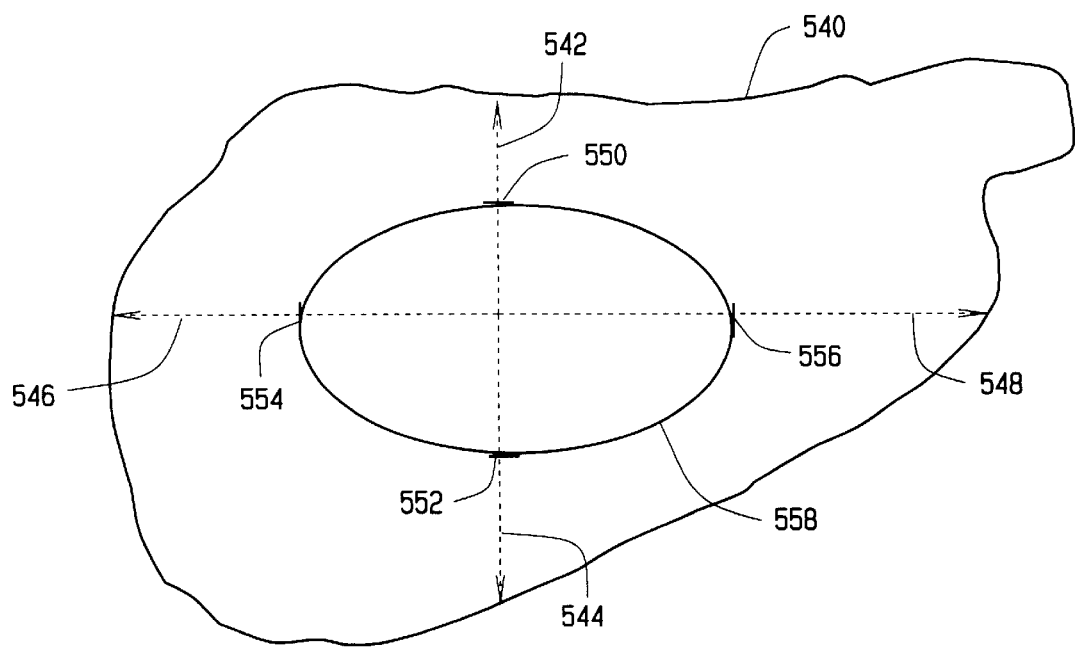
FIG. 5a is a representation of using an ellipse to calculate a new center of gravity and a second ribeye contour.

The ellipse into the ribeye functional block 522 is representative of the step to calculate a new center of gravity from the first ribeye contour. From the previously established center of gravity the method extends outward in four directions (north, south, east and west) until the ribeye contour (see FIG. 5A, Item 540) is hit as represented in FIG. 5A by lines 542, 544, 548, and 546 respectively. This provides a horizontal and vertical size of the inside of the first ribeye contour. By using a predetermined factor (for example, 0.5) to these dimensions as identified by 550, 552, 554, and 556 of FIG. 5A, we put an ellipse 558 around the center of gravity. This ellipse is created using the 0.5 factor in order to never hide the ribeye contour. Other factors could be utilized when appropriate, particularly for other meat cuts. Inside the ellipse all fat classed pixels are changed to be classed Lean. This helps to clear at this step a lot of marbling for a better ribeye contour search in the next steps. (Later for marbling determination the cleared fat areas are used again so there is no missing marbling.) An ellipse is utilized in this functional step because an ellipse closely approximates the shape of a ribeye, however, other closed curve geometries can be utilized.

The determination of the second ribeye contour functional block 524 performs a similar operation as functional block 520 determining a second adaptive gradient, but with the ellipse around the center only has lean classified pixels inside when determining this second ribeye contour.

The second erode and dilate functional block 526 performs the same type of erosion and dilation as performed by functional block 512, but for the second adaptive ribeye contour instead of the preliminary outside contour. With this method we cut off attached muscles. However, this dilatation differs from block 512 in that this dilation will go with a higher number of steps than the erosion to lay a band around the ribeye for the third ribeye contour search. This may be necessary due to the loss of accuracy of the contour due to erosion.

The determination of the third adaptive ribeye contour functional block 528 performs the same function as functional block 520 determining a third adaptive gradient. However, the ellipse around the center has only lean classified pixels inside the ellipse and the attached muscles are cut off.

Figure 5B:
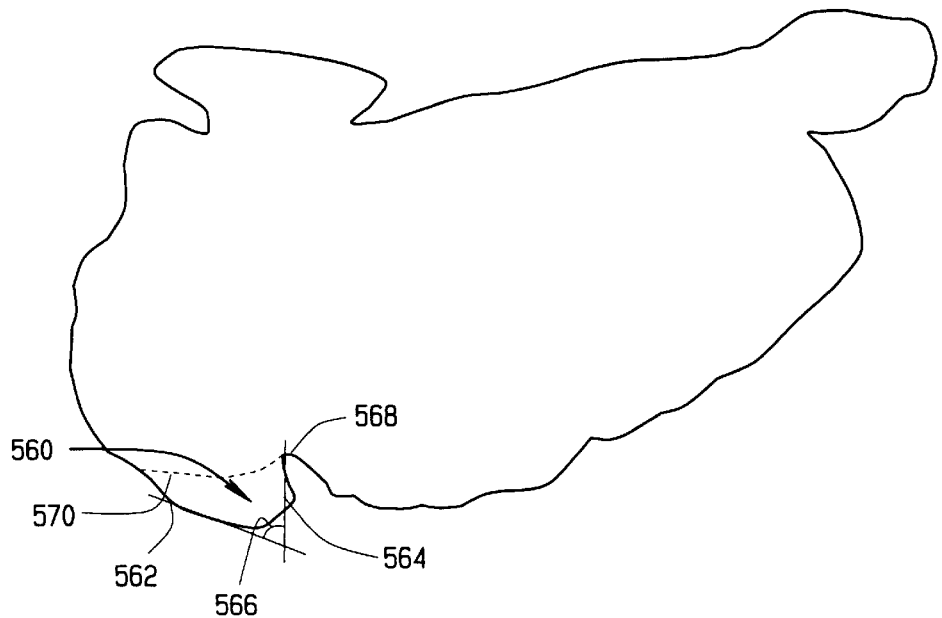
FIG. 5b is a representation of the method of cutting undesired corners and edges.

The search for corners/edges functional block 530 cleans up any undesired attached adjacent muscle that remains after functional blocks 524 to 528 have been performed. The method examines the third adaptive ribeye contour looking for corners (see FIG. 5B, 560) that may indicate an undesired attached muscle in the following way. An actual location on the ribeye contour where there is an outward protruding contour is identified and on either side of the contour first and second straight lines (see FIG. 5B, 562 and 564) are utilized to linearly approximate the curve of the contour and the lines have a predetermined length and the lines are positioned on the ribeye contour in a frontward and backward manner such that they intersect forming an angle 566. The predetermined length must be long enough to adequately approximate the typical contour. For example, when utilizing a camera having a 768×572 pixel resolution for capturing a ribeye, first and second approximation lines 20 pixels long should be long enough to approximate and intersect. For example, the angle between the lines should be approximately 180° or a substantially flat contour. If the angle between the lines is smaller than a predetermined level (90°) then the method assumes an undesired corner where there could still be an undesired attached muscles. The predetermined 90° angle could vary depending on the meat cut. Along a predetermined angle from the corner point we search now for an opposite contour point 568 that would cut off the attached muscle. The corner point is determined from the intersection of the two lines. However, before the method cuts off the corner/edge the method can preferably check different plausibility factors that should indicate if the corner is an undesired attached muscle or not. If the plausibility factors indicate undesired muscle, the method cuts off the undesired muscle using a circular pattern to cut off the corner/edge leaving a circular contour or a curved cut line. One plausibility factor could be examining the ratio between the square of the lengths of the curved cut line over the area cut off. If the ratio is small, then the area being cut can be large relative to the ribeye area which can verify that it is an adjacent muscle. If the ratio is large, then the area being cut can be small relative to the ribeye area which can indicate it is not an adjacent muscle. A second plausibility factor could be the length of the curved cutting line relative to the height of the ribeye. For example, if the cutting line is longer than the typical quarter of the height of a ribeye, then it is likely an adjacent muscle. A third plausibility factor could be the number of lean pixels as compared to the fat pixels in the cut off area. If a much larger percentage of fat pixels, then this may verify the likelihood of cut off area being adjacent muscle. Once the corners/edges function is complete, the final ribeye contour is defined.

The counting lean and fat pixels in ribeye functional block 532 calculates the following parameters:

ribeye area lean area in ribeye fat area in ribeye unknown area in ribeye number of fat objects in ribeye average size of fat objects number of gradients between lean and fat horizontal and vertical in the ribeye correction of number of fat areas (big fat pieces are not counted)

color measurement of all lean pixels for lean color

The fat strip functional block 534 determines a subcutaneous fat area positioned between $5/8$ and $7/8$ along the axis of the ribeye and orthogonal to the ribeye contour and the following parameters are calculated:

area of fat average fat thickness once the above parameters have been calculated, the algorithm can insert the parameters into regression formula for calculating meat quality and yield grade Referring to FIG. 6, a flow diagram of the color segmentation portion of the algorithm is shown. This flow diagram outlines the adaptive method for color classification of pixels within the image. This adaptive method is important because the color of lean and fat can vary from carcass to carcass. For example, some carcasses may have a ribeye cross section where the lean portion is a darker red than other carcasses. Another example is that the fat surrounding the ribeye cross section of a beef carcass can sometimes have a reddish hue as opposed to other carcasses where the fat is closer to a true white. The variation in lean and fat color from carcass to carcass make it difficult to predefine a color range for fat or lean. Therefore, this adaptive method was developed to allow color classification to adapt to the lean color and fat color of a given carcass. The functional flow diagram in FIG. 6 outlines the steps in the algorithm for this adaptive color classification method. Functional blocks 602 and 604 search the image to locate the brightest and darkest areas of the image. The color of the brightest area is utilized to define the start point or center point in the RGB color space for pixels to be classified as fat pixels. The color of the darkest area of the image is utilized to define the start point or center point in the RGB color space for pixels to be classified as background pixels. The color start point in the RGB color space for lean will be estimated to be between the two start points for fat and background. The functional steps for establishing the start points in the RGB color space is defined by functional blocks 606 and 608. Functional block 610 represents the nearest neighbor functional step which classifies each pixel as lean, fat, background or unknown. The pixels are classified based on the closest start point in the RGB color space. However, if a given pixel is nearly the same distance to at least two of the start points, then the pixel will be classified as unknown as outlined above. Once the color classification is completed, the outside contour of a cutting surface is determined as represented by functional block 612 and further, functional block 612 determines the center of gravity based on the outside contour determined in this step. Functional block 614 defines a rectangular subarea about the center of gravity determined by functional block 612 and determines the average lean color within the rectangle, thereby redefining the lean color start point within the RGB color space. As noted above, a subarea having any geometry can be utilized. Functional block 616 represents the adaptive reclassification of the start points for lean, fat and background in the RGB color space. This method provides a more accurate color classification than other methods currently utilized. An accurate color classification is critical for the steps of defining the contour using the method of detecting a gradient from one classification to another.

Figure 7:
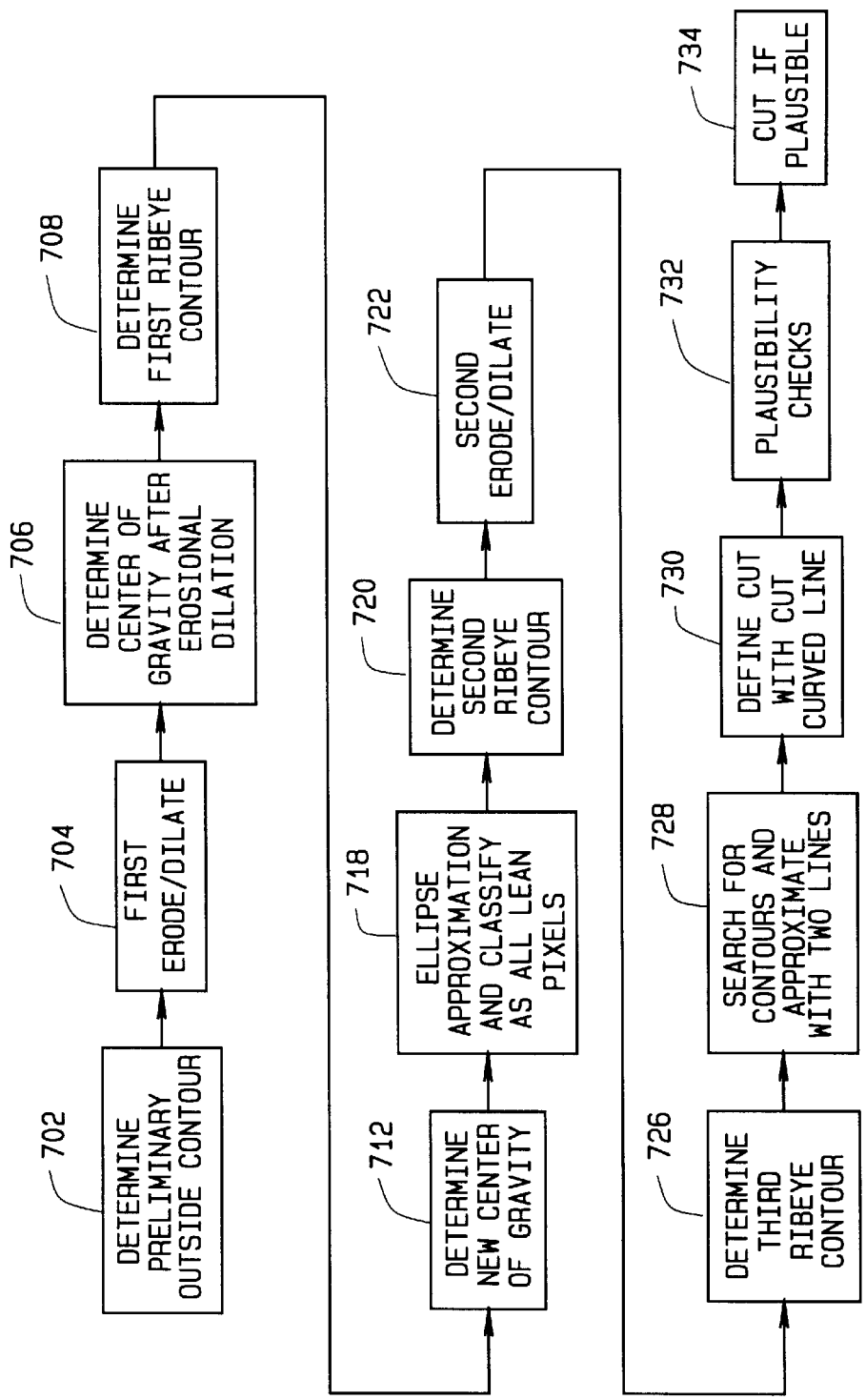
FIG. 7 is a detailed flow diagram of the contour determination portion of the algorithm.

Referring to FIG. 7, a detailed flow diagram of the contour determination portion of the algorithm is shown. Functional block 702 represents the functional step of determining the preliminary outside contour by starting from the border of the image working inward and detecting gradients between background and non-background pixels. Once the preliminary outside contour has been defined utilizing the gradient method of functional block 702, erosion and dilation of the image is performed by functional block 704. Once the first erosion and first dilation 704 occurs, a new outside contour is defined and further, functional block 706 defines the center of gravity based on that new outside contour. Functional block 708 is representative of determining the first ribeye contour by starting from the center of gravity and working outward looking for gradient between lean and non-lean thereby defining the first ribeye contour. A new center of gravity is determined based on the first ribeye contour and this functional step is represented by functional block 712. Functional block 718 defines an ellipse about the new center of gravity and within the ellipse defines all pixels as lean. This facilitates determining the contour of the lean utilizing gradients. This is performed by starting from the center of gravity and working outward to determine gradients between the all lean pixel within ellipse and non-lean pixels. This gradient method is defined by functional block 720 which determines and defines a new second ribeye contour. Functional block 722 performs similar erosion and dilation as step 704 except dilation will be with a higher number of steps than the erosion. A third ribeye contour is then determined by functional block 726 by performing a similar method as functional block 720. Functional blocks 728 and 730 search for contours that are not part of the ribeye and defines a curved cutting line to cut them off. Plausibility checks as outlined herein can be performed as represented by functional block 732. If Plausibility checks confirm that a contour is not part of ribeye, then a cut is performed as represented by functional block 734.

The various image analysis grading system examples shown above illustrate a novel image analysis grading apparatus and method. A user of the present invention may choose any of the above image analysis grading apparatus or method embodiments, or an equivalent thereof, depending upon the desired application. In this regard, it is recognized that various forms of the subject image analysis grading invention could be utilized without departing from the spirit and scope of the present invention.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present invention.

Other aspects, objects and advantages of the present invention can be obtained from the study of the drawings, the disclosure and the appended claims.

INDUSTRIAL APPLICABILITY

The present invention has significant industrial applicability. As described herein, many meat processing facilities still utilize human graders to grade the quality of meat from a beef carcass or to predict lean meat yield from a carcass. However, the methods utilized by human graders are very subjective. This subjectivity can have an adverse financial effect on the meat processing facility as outlined herein. Due to the subjective nature of grading by human graders, image analysis systems have been developed to automatically grade the beef carcass. However, image analysis systems prior to this invention have had problems reliably grading a beef carcass.

One aspect of the present invention is its ability to consistently capture a good image of the ribeye cross section. This is made possible by the substantially wedge-shaped camera design that allows the user to readily insert the camera into the incision of the ribbed carcass. Also, the camera design includes various alignment means to facilitate accurate and consistent alignment of the camera prior to capturing the image. The wedge-shaped camera design and the alignment means allow the user to consistently capture a good image, even when the incision of the ribbed carcass is shorter than the norm, making it difficult even for human graders to examiner the ribeye cross section. The wedge-shaped camera with alignment means makes it easy for the user to insert the camera into the incision consistently capturing good images.

The present invention also addresses the issue of inconsistent or inadequate lighting in a beef processing facility. The hood-shaped camera design creates an isolated image capturing environment such that a camera flash can control the lighting for the image. Further, the image analysis computing system can accommodate various carcasses having inconsistent lean and fat color from carcass to carcass. The adaptive color segmentation method of the present invention allows the present invention to adapt to each unique carcass.

The camera housing can be manufactured in stainless steel making for easy cleanup. Also, the camera housing can be a two-piece design such that the top portion of the housing is removably attached to the bottom base portion such that cleaning can be facilitated. Also, the handle design is ergonomically placed and shaped for easy handling and positioning of the camera. The handle can be designed with an integral trigger that allows the user to trigger the shutter of the camera and the camera flash. The ergonomic design of the handle allows the user to manipulate and position the camera with one hand while triggering the capturing of the image with the same hand.

The camera can be communicably linked to a mobile work station that comprises the image analysis computing means, as well as a monitor for viewing the image. The work station, as well as the image analysis computing system and monitor, can be organized appropriately for the meat processing work environment. The image analysis computing system could be a standard personal computer based system having the appropriate software installed. The camera and work station design allows the user to operate in a production meat processing environment while rapidly grading each carcass and storing the data to the image analysis computing system for later review and analysis. The present invention provides for an objective grading system that is designed to operate in a production meat processing facility and further designed to provide a consistent and reliable grading means.

What is claimed is:

1. An animal carcass grading system for predicting quality and meat yield comprising:
   an image capturing camera assembly further comprising,
   a substantially wedged-shaped housing having a flat bottom side, said bottom having a viewing window;
   a camera contained in said housing where the field of view of said camera is canted downward to at least subtend the viewing window, said camera having a camera image output and a camera flash;
   a trigger communicably linked to the camera flash and camera and said trigger operable to trigger the camera to capture an image and further operable to trigger the camera flash; and
   where said camera image output is operable to output the image captured for input to an image analysis computing system.

2. An animal carcass grading system as recited in claim 1 where the flat bottom of said housing further comprises first and second guide extensions attached thereto and extending below the exterior surface of the flat bottom and disposed on opposing sides of the viewing window for aligning the viewing window side-to-side.

3. An animal carcass grading system as recited in claim 2 where the flat bottom of said housing further comprises a back stop guide extension attached thereto and extending below the exterior surface of the flat bottom and disposed to one side of the viewing window for positioning to the viewing window front to back.

4. An animal carcass grading system as recited in claim 3 where the wedge-shaped housing has a handle extending from the bottom and where said trigger is integral with said handle.

5. An animal carcass grading system as recited in claim 1 where said camera is an analog camera further comprising frame grabber circuitry operable to digitize the analog image captured.

6. An animal carcass grading system as recited in claim 1 where said camera is a digital camera.

7. An animal carcass grading system as recited in claim 1 where said camera flash extends substantially around the lens of the camera.

8. An animal carcass grading method for predicting quality and yield comprising the steps of:
   providing an image capturing camera assembly further comprising the steps of,
   enclosing a camera in a substantially wedged-shaped housing where said housing has a flat bottom, where said bottom has a viewing window and where the field of view of said camera is canted downward to at least subtend the viewing window;
   placing the viewing window over an object to be captured;
   flashing with a camera flash and capturing an image of the object with the camera; and
   outputting the image through a camera image output operable to output an image to an image analysis computing system operable to grade the image.

9. The animal carcass grading method for predicting as recited in claim 8 where placing the viewing window is placing the viewing window using first and second guide extensions attached to said housing and extending below the exterior surface of the flat bottom and disposed on opposing sides of the viewing window operable for aligning side-to-side placement.

10. An animal carcass grading method for predicting quality and yield as recited in claim 9 where placing the viewing window is placing the viewing window using a back stop guide extension attached to said housing operable for aligning front to back placement.

11. An animal carcass grading method for predicting quality and yield as recited in claim 8 where capturing an image is capturing an analog image and said grading method further comprising the step of grabbing a frame with a frame grabber circuit operable to digitize the analog image captured.

12. An animal carcass grading method for predicting as recited in claim 8 where capturing an image is capturing a digital image.

13. An animal carcass grading method for predicting as recited in claim 8 where flashing with a camera flash is flashing with a camera flash that extends substantially around the lens of the camera.

* * * * *